(12) United States Patent
De Boer

(10) Patent No.: US 11,197,648 B2
(45) Date of Patent: Dec. 14, 2021

(54) DOCKING VIEWING SYSTEM FOR MOBILE X-RAY SYSTEMS

(71) Applicant: KONINKLIJKE PHILIPS N.V., Eindhoven (NL)

(72) Inventor: Jacob De Boer, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 416 days.

(21) Appl. No.: 16/336,493

(22) PCT Filed: Sep. 30, 2017

(86) PCT No.: PCT/EP2017/074923
§ 371 (c)(1),
(2) Date: Mar. 26, 2019

(87) PCT Pub. No.: WO2018/060511
PCT Pub. Date: Apr. 5, 2018

(65) Prior Publication Data
US 2021/0275117 A1  Sep. 9, 2021

(30) Foreign Application Priority Data
Sep. 30, 2016 (EP) .................................... 16191646

(51) Int. Cl.
*A61B 6/00* (2006.01)
(52) U.S. Cl.
CPC ............ *A61B 6/4405* (2013.01); *A61B 6/462* (2013.01)

(58) Field of Classification Search
CPC .............................. A61B 6/4405; A61B 6/462
See application file for complete search history.

(56) References Cited

U.S. PATENT DOCUMENTS

| 5,712,482 A * | 1/1998 | Gaiser .................. A61B 6/4405 |
| | | 378/189 |
| 6,007,243 A | 12/1999 | Ergun |
| 6,256,374 B1 | 7/2001 | Tomasetti |

(Continued)

FOREIGN PATENT DOCUMENTS

| CN | 104398265 A | 3/2015 |
| DE | 102011005439 A1 | 9/2012 |

(Continued)

*Primary Examiner* — Chih-Cheng Kao

(57) ABSTRACT

The present invention relates to mobile X-ray imaging. In order to provide a mobile display system for X-ray imaging with improved space requirements, a mobile medical imaging viewing station (14) is provided. The mobile medical imaging viewing station comprises a mobile support stand (30), a display device (32) movably mounted to the support stand, and a docking arrangement (34). The display device is movable to provide adapted positioning of the display device in relation to the mobile support stand. The docking arrangement comprises a docking interface attached to the support stand. The docking arrangement is configured to interact with a counter-interface of a mobile medical X-ray imaging station for docking the mobile medical imaging viewing station to a mobile X-ray imaging station for at least transport purposes. The mobile support stand is provided with wheels (38) that are retractable when the docking to a mobile medical X-ray imaging station is provided.

9 Claims, 3 Drawing Sheets

(56) References Cited

U.S. PATENT DOCUMENTS

| | | | |
|---|---|---|---|
| 8,000,446 B2 | 8/2011 | Van | |
| 2008/0198968 A1* | 8/2008 | Takekoshi | A61B 6/4441 |
| | | | 378/62 |
| 2010/0002844 A1 | 1/2010 | Van Woezik | |
| 2011/0317816 A1* | 12/2011 | Bechard | A61B 6/56 |
| | | | 378/98.8 |
| 2012/0093298 A1* | 4/2012 | Lalena | A61B 6/464 |
| | | | 378/198 |
| 2013/0300271 A1 | 11/2013 | Reina | |
| 2014/0233702 A1* | 8/2014 | Suzuki | A61B 6/547 |
| | | | 378/62 |
| 2014/0233703 A1* | 8/2014 | Omura | A61B 6/4405 |
| | | | 378/98 |
| 2015/0350545 A1 | 12/2015 | Welsh | |

FOREIGN PATENT DOCUMENTS

| | | |
|---|---|---|
| JP | 2004313739 A | 11/2004 |
| JP | 2009253701 A | 10/2009 |
| JP | 2011156287 A | 8/2011 |
| JP | 2016174797 A | 10/2016 |
| WO | 2007046041 A2 | 4/2007 |

\* cited by examiner

US 11,197,648 B2

DOCKING VIEWING SYSTEM FOR MOBILE X-RAY SYSTEMS

CROSS-REFERENCE TO PRIOR APPLICATIONS

This application is the U.S. National Phase application under 35 U.S.C. § 371 of International Application No. PCT/EP2017/074923, filed on Sep. 30, 2017, which claims the benefit of European Patent Application No. 16191646.5, filed on Sep. 30, 2016. These applications are hereby incorporated by reference herein.

FIELD OF THE INVENTION

The present invention relates to mobile X-ray imaging, and relates in particular to a mobile medical imaging viewing station and to a mobile medical X-ray imaging system.

BACKGROUND OF THE INVENTION

During medical examinations or interventions, e.g. surgery, mobile X-ray systems are used to provide X-ray images of, for example, a current situation. The images generated during X-ray examinations may be displayed on a monitor or display to provide visible information, e.g. about what has been executed during a surgery activity or as live imaging. This viewing function may be provided on a separate system, e.g. second system, which must also be mobile for transport and positioning. For example, US 2010/0002844 describes a mobile stand with movably mounted monitors. However, it has been shown that additional display systems need space that is becoming more and more used by further devices.

SUMMARY OF THE INVENTION

There may be a need to provide a mobile display system for X-ray imaging with improved space requirements.

The object of the present invention is solved by the subject-matter of the independent claims; further embodiments are incorporated in the dependent claims. It should be noted that the following described aspects of the invention apply also for the mobile medical imaging viewing station and for the mobile medical X-ray imaging system.

According to the present invention, a mobile medical imaging viewing station is provided that comprises a mobile support stand, a display device movably mounted to the support stand, and a docking arrangement. The display device is movable to provide adapted positioning of the display device in relation to the mobile support stand. Further, the docking arrangement comprises a docking interface attached to the support stand, the docking arrangement configured to interact with a counter-interface of a mobile medical X-ray imaging station for docking the mobile medical imaging viewing station to a mobile X-ray imaging station for at least transport purposes. Still further, the mobile support stand is provided with wheels that are movable to be lifted when the docking to a mobile medical X-ray imaging station is provided in order to avoid contacting a floor surface.

The docking is also referred to as temporarily fixation. The docking comprises a positioning and fixating of the mobile medical imaging viewing station to the mobile X-ray imaging station.

The mobile medical imaging viewing station is thus provided as a docking viewing system (DVS).

The docking functionality provides an easier handling during movement and allows a space saving movement and also storing. This greatly improves the spatial situation in an examination room, e.g. in a hospital. The docking can be provided in particular for transport and storing purposes. However, it is also provided that the mobile medical imaging viewing station can maintain attached to the mobile medical X-ray imaging station for viewing purposes, e.g. during X-ray imaging.

The movable, i.e. liftable wheels provide movability for the viewing station when not attached to the imaging system, i.e. the liftable wheels allow independent movement of the viewing station. The liftable wheels also provide an easier movement of the complete mobile system, i.e. the system comprising the two mobile stations for imaging and viewing, when attached to the imaging station. The movability and hence the mobility of the whole system is thus facilitated and improved.

According to an example, the wheels are retractable when the docking to a mobile medical X-ray imaging station is provided.

In another example, docking guides are provided on the side of a mobile medical X-ray imaging station and the docking guides, i.e. mechanical guides, lift or retract the wheels of the docking viewing system from the ground floor. In an example, during the docking, the wheels of the viewing system are moved upon the mechanical guides, i.e. they run over the mechanical guides.

According to an example, a handlebar is provided that is attached to the mobile support stand to manually move the mobile medical imaging viewing station; wherein the handlebar is also provided as a handlebar for moving a mobile medical X-ray imaging system when the temporarily fixing to a mobile medical X-ray imaging station is provided.

According to an example, the mobile support stand comprises a space for accommodating the display device during docking.

According to an example, the mobile support stand is provided L-shaped. A lower base part extends horizontally and provides a support frame for the retractable wheels. An upright part extends vertically and provides the space for accommodating the display device during transport in the docked position.

According to the invention, also a mobile medical X-ray imaging system is provided that comprises a mobile X-ray imaging station with an X-ray source and an X-ray detector mounted to a mobile support stand. Further, a mobile imaging viewing station according to one of the above-mentioned examples is provided. The X-ray images acquired by the mobile imaging station are shown on the mobile imaging viewing station. Furthermore, the mobile imaging viewing station is attachable to the mobile support stand via the interface for common movement of both the mobile X-ray imaging station and the mobile imaging viewing station.

According to an example, the mobile support stand of the mobile medical imaging viewing station is having an abutting side adapted to conform with an abutting side of the mobile support stand of the mobile X-ray imaging station.

The mobile medical imaging viewing station is also referred to as mobile viewing station; the mobile medical X-ray imaging station is also referred to as mobile X-ray station or mobile imaging station.

The mobile medical X-ray imaging system is also referred to as mobile imaging system.

According to an aspect, it is provided to mechanically connect (dock) a viewing system during transport and storage with a mobile (surgery) X-ray system. When the viewing system is docked on the mobile X-ray system, it can be transported and stored as one system. This results in that the operator can much easier transport and store the mobile surgery X-ray system with the docked viewing system. During practical use, the docking viewing system will be taken of, i.e. undocked, and positioned near the area of interest, e.g. a patient and patient table. The display or display can be positioned close to the area of interest. As an effect, the operator can conveniently directly see on the viewing system what is happening and how the procedure proceeds. The display may be stored inside the docking viewing system; the display can be shifted out of the stored situation and can then be rotated and tilted to achieve the most optimized position near the patient and patient table.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
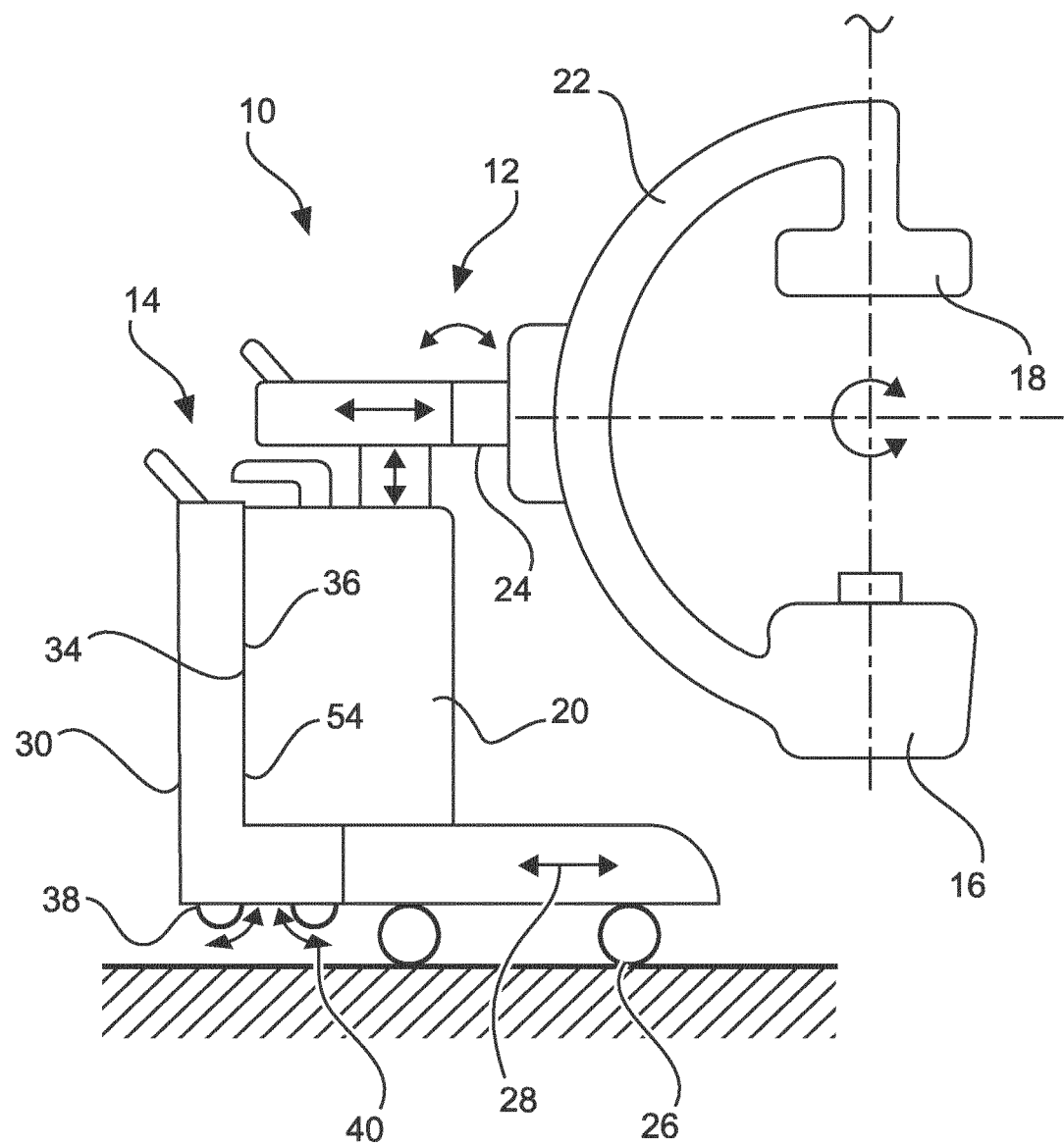
FIG. 1 shows an example of a mobile medical X-ray imaging system with a mobile X-ray imaging station and a docked mobile imaging viewing station in a side view.

FIG. 1 shows a mobile medical X-ray imaging system 10. The mobile medical X-ray imaging system 10 comprises a mobile X-ray imaging station 12 and a mobile imaging viewing station 14. The mobile imaging viewing station 14 will also be described in more details below with reference to the further drawings.

The mobile X-ray imaging station 12 comprises an X-ray source 16 and an X-ray detector 18 that are mounted to a mobile support stand 20. For example, the support stand 20 comprises a C-arm 22 for movably supporting the X-ray source 16 and the X-ray detector 18. The C-arm may be mounted by a movable support structure 24. Further, a movement structure, e.g. wheels 26 are provide to allow movement of the mobile X-ray imaging station 12, for example in an examination room. The movement along the room is indicated with a double arrow 28. The movement of the C-arm 20 is indicated with further arrows.

It is noted that also other types of systems are provided as the mobile X-ray imaging station 12. For example, mobile systems with fixedly mounted X-ray sources are provided. Further, independent X-ray detectors can be provided.

The mobile X-ray imaging station 12 is configured to acquire and provide X-ray images, which can then be shown on the mobile imaging viewing station 14.

Figure 3:
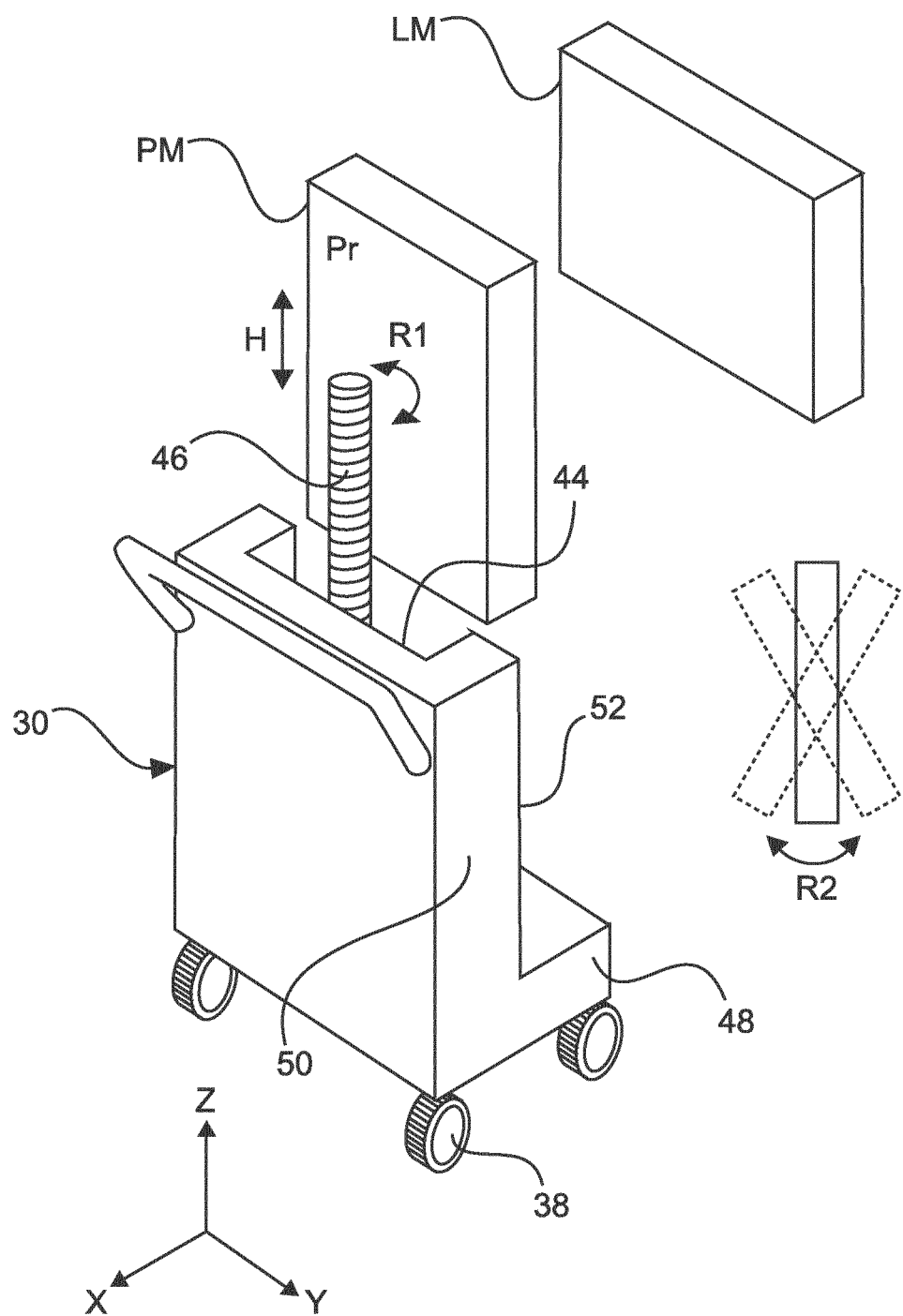
FIG. 3 shows another example of the mobile imaging viewing station of FIG. 2.

The mobile medical imaging viewing station 14 is shown having a mobile support stand 30, see also the following figures. Further, a display device 32 is movably mounted to the support stand 30. Still further, a docking arrangement 34 is provided. The display device 32 is arranged movable to provide adapted positioning of the display device 32 in relation to the mobile support stand 30. This is shown in FIG. 3.

The docking arrangement 34 comprises a docking interface (not shown in detail) attached to the support stand 30. The docking arrangement 34 is configured to interact with a counter-interface of a counter-docking arrangement 36 of the mobile medical X-ray imaging station 12 for docking the mobile medical imaging viewing station 14 to the mobile X-ray imaging station 12 for at least transport purposes. For movement, e.g. across an examination room, both stations can be attached to each other to allow common moving of both. In FIG. 1 the mobile imaging viewing station 14 is attached to the mobile support stand 20 of the mobile X-ray imaging station 12 via the interface 34 for common movement of both the mobile X-ray imaging station 12 and the mobile imaging viewing station 14.

Figure 2:
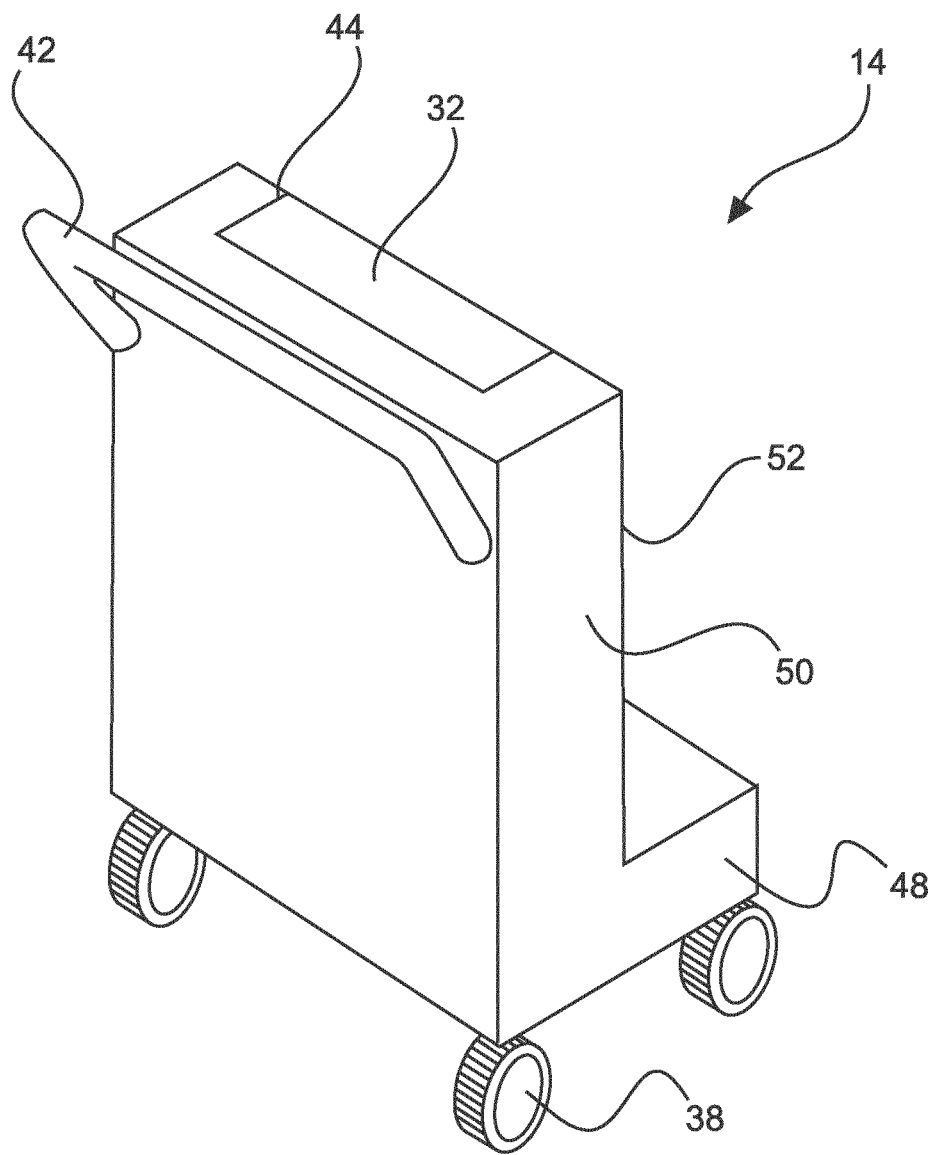
FIG. 2 shows an example of the mobile imaging viewing station of FIG. 1 in a perspective view.

FIG. 1 shows a docked state of the mobile medical imaging viewing station 14, and FIG. 2 shows an un-docked state of the mobile medical imaging viewing station 14.

As can be seen in FIGS. 1 and 2, the mobile support stand 30 of the mobile medical imaging viewing station 14 is provided with wheels 38 that are movable to be lifted when the docking to a mobile medical X-ray imaging station is provided in order to avoid contacting a floor surface. In FIG. 1, arrows 40 indicate a movement of the wheels, e.g. a retraction.

In an example, the wheels 38 are retractable when the docking to a mobile medical X-ray imaging station is provided.

Retracting the wheels, the mobile imaging viewing station is so-to-speak carried by the mobile X-ray imaging station in the docked state. The maneuverability is improved with retracted wheels and can be done by one operator.

In another example, not shown, the wheels of the mobile medical imaging viewing station run on guide ways achieving the results that the wheels will be "retracted" from the ground floor.

In an example, not further shown in detail, the display device is provided as a monitor. In another example, the display device is provided as a touch-sensitive display device, i.e. a touchscreen. In another example, the display device is provided as a display arrangement comprising a plurality of display devices, for example two or three display devices like monitors or touchscreens.

In an example, also not further shown in detail, a printer or other communication or data related devices like a CD- or DVD player/reader are provided by the support stand.

For secure positioning, the mobile medical imaging viewing station 14 is provided with a floor brake mechanism, e.g. the mobile support stand 30 comprises e.g. retractable supports for resting on the floor for parking purposes. In another example, the wheels are provided with brakes. In other words, for example, braking elements are provided to interact directly with the floor surface. In another example, braking elements are provided that act on the wheels.

As a further option, the mobile medical imaging viewing station 14 is equipped with a handlebar 42 that is attached to the mobile support stand 30. Thus, the mobile medical imaging viewing station 14 can be moved manually. The handlebar 42 may also be provided as a handlebar for moving the mobile medical X-ray imaging system 10 when the temporarily fixing of the mobile medical imaging viewing station 14 to the mobile medical X-ray imaging station 12 is provided.

As indicated in FIG. 3, in an example, as an option the display device 32 is movably mounted such that it can be positioned vertically to allow for different height positioning of the display device. As a further option, additionally or alternatively, the display device 32 is movably mounted such that it can be tilted around a horizontal axis to allow inclined positioning of the display device. As a further option, additionally or alternatively, the display device 32 is movably mounted such that it can be rotated around a horizontal axis to allow different orientation of a rectangular display field. The positioning may comprise rotating the screen around a first horizontal axis which is running in a first direction towards/from the viewer, e.g. to be able to arrange a rectangular display area in a landscape LM or portrait manner PM. The first horizontal axis is also referred to as X-axis, and the first rotation around that axis as $R_X$ rotation. The positioning may also comprise rotating the screen around a second horizontal axis which is running in a second direction across the first direction, i.e. across a direction towards/from the viewer, e.g. perpendicular to the viewing direction, e.g. can also be tilted around the Y-axis so it's optimal positioned for the user to have a view optimum view on the Screen. The second horizontal axis is also referred to as Y-axis, and the rotation around that axis as $R_Y$ rotation. The positioning may also comprise rotating the screen around a vertical axis, e.g. to be able to get it closer the area of interest. The vertical axis is also referred to as Z-axis, and the rotation around that axis as $R_Z$ rotation. In FIG. 3, the three axis are schematically indicated.

As a further option, the mobile support stand 30 of the mobile medical imaging viewing station 14 comprises a space 44 for accommodating the display device 32 during docking. In an example, the display device 32 is slidably mounted on the viewing station on a vertical guide 46 with a balancing mechanism (not shown). In the docked position, the display device 32 can thus be fully retracted into the mobile medical imaging viewing station 14. In this situation, it is protected for mechanical impact to protect for damaging and realize maximum view during transportation of the mobile medical imaging viewing station, so it is not restricting the operators view during transport.

As a still further option, the mobile support stand 30 of the mobile medical imaging viewing station 14 is provided to be L-shaped. A lower base part 48 extends horizontally and provides a support frame (not shown) for the retractable wheels 38, and wherein an upright part 50 extends vertically and provides the space for accommodating the display device during transport in the docked position. In an example, the L-shape relates to a support structure or frame, and may also comprise the shape of a housing.

In an example, the mobile support stand 30 of the mobile medical imaging viewing station 14 is having an abutting side 52 adapted to conform with an abutting side 54 of the mobile support stand 20 of the mobile X-ray imaging station 12. The abutting may result in completed outer shape as shown in FIG. 1.

The display device 32 may be provided to be movable in relation to the support stand 30 in at least one of the following ways. The display device 32 can be adjusted in height H by a vertical movement (indicated with a double arrow), in its orientation by a first rotation R1 (indicated with a further double arrow), and also in its inclination by a second rotation R2 (indicated with a still further double arrow). The orientation change and the inclination change are shown in FIG. 3.

As mentioned, the docking viewing system contains a docking mechanism so it can be positioned and fixated onto the Mobile Surgery X-ray system. When the docking viewing system is docked onto the mobile surgery X-ray system, its wheels will be retracted. This means during transport only the wheels of the mobile surgery X-ray system are in contact with floor. This has an advantage in that transport will be easier with one integrated system, especially when passing doorsteps, but also during maneuvering in back, forward, left and right directions. Once taken of, i.e. un-docked, the docking viewing system can be positioned in the operating area since it has its own positioning wheels to position it close to the patient and patient table. The display(s) have a suspension/guiding mechanism so it's easy to position it close to the area of interest directly where the operator wants to have it located. As indicated, the display(s) can also have a touch screen functionality to execute display functionalities or activate Mobile Surgery functions. To position the display(s), a vertical guiding with balancing mechanics may be used to realize low handling forces for the vertical height positioning, once in upper position the display(s) can be rotated from portrait to landscape and 180° rotated in the horizontal plane. Small tilt rotation is possible in the vertical plane to realize an optimal view on the display(s).

The system can be handled, i.e. transported and maneuvered, by one person and the docking viewing system can be easily docked and un-docked. With its own transport mechanism, the docking viewing system can be positioned very easy in the operating area.

It has to be noted that embodiments of the invention are described with reference to different subject matters. In particular, some embodiments are described with reference to a mobile medical imaging viewing station, whereas other embodiments are described with reference to mobile medical X-ray imaging system. However, a person skilled in the art will gather from the above and the following description that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A mobile medical imaging viewing station, comprising:
    a mobile support stand;
    a display device movably mounted to the mobile support stand; and
    a docking arrangement;
    wherein the display device is movable to provide adapted positioning of the display device in relation to the mobile support stand;

wherein the docking arrangement comprises a docking interface attached to the mobile support stand, the docking arrangement configured to interact with a counter-interface of a mobile medical X-ray imaging station for docking the mobile medical imaging viewing station to the mobile medical X-ray imaging station for at least transport purposes; and wherein the mobile support stand is provided with wheels that are movable to be lifted when the docking to the mobile medical X-ray imaging station is provided in order to avoid contacting a floor surface.

2. The mobile medical imaging viewing station according to claim 1, wherein the wheels are retractable when the docking to the mobile medical X-ray imaging station is provided.

3. The mobile medical imaging viewing station according to claim 1, wherein the mobile support stand comprises a floor brake mechanism.

4. The mobile medical imaging viewing station according to claim 1, wherein a handlebar is provided that is attached to the mobile support stand to manually move the mobile medical imaging viewing station; wherein the handlebar is also provided as a handlebar for moving a mobile medical X-ray imaging system when temporarily fixing to the mobile medical X-ray imaging station is provided.

5. The mobile medical imaging viewing station according to claim 1, wherein the display device is movably mounted such that it can be:
   i) positioned vertically to allow for different height positioning of the display device; and/or
   ii) tilted around a horizontal axis to allow inclined positioning of the display device; and/or
   iii) rotated around a horizontal axis to allow different orientation of a rectangular display field.

6. The mobile medical imaging viewing station according to claim 5, wherein the mobile support stand comprises a space for accommodating the display device during docking.

7. The mobile medical imaging viewing station according to claim 6, wherein the mobile support stand is provided L-shaped, wherein a lower base part extends horizontally and provides a support frame for the wheels, and wherein an upright part extends vertically and provides the space for accommodating the display device during transport in a docked position.

8. A mobile medical X-ray imaging system comprising:
   a mobile X-ray imaging station with an X-ray source and an X-ray detector mounted to a mobile support stand; and
   a mobile medical imaging viewing station according to claim 1;
   wherein the X-ray images acquired by the mobile X-ray imaging station are shown on the mobile medical imaging viewing station; and
   wherein the mobile medical imaging viewing station is attachable to the mobile support stand of the mobile X-ray imaging station via an interface for common movement of both the mobile X-ray imaging station and the mobile medical imaging viewing station.

9. The mobile medical X-ray imaging system according to claim 8, wherein the mobile support stand of the mobile medical imaging viewing station is has an abutting side adapted to conform with an abutting side of the mobile support stand of the mobile X-ray imaging station.

* * * * *